United States Patent [19]

Monsod, Jr.

[11] 4,251,508

[45] Feb. 17, 1981

[54] PROCESS FOR EXTRACTING VALUABLE NUTRIENTS FROM THE LEAVES OF THE WATER LILY OR WATER HYACINTH PLANT

[76] Inventor: Godofredo G. Monsod, Jr., 11 Scout Bayoran Street, Quezon City, Philippines

[21] Appl. No.: 935,664

[22] Filed: Aug. 21, 1978

Related U.S. Application Data

[63] Continuation-in-part of Ser. No. 702,612, Jul. 6, 1976, abandoned.

[30] Foreign Application Priority Data

Mar. 25, 1976 [PH] Philippines .................................. 9876

[51] Int. Cl.$^3$ ...................... A61K 35/78; A61L 13/00
[52] U.S. Cl. ........................................ 424/76; 424/195; 424/252; 424/255; 424/266; 424/344
[58] Field of Search ................................. 424/195, 76

[56] References Cited

U.S. PATENT DOCUMENTS 1,568,339   1/1926   Leftwich ............................. 426/635

OTHER PUBLICATIONS

Hyacinth Control Journal, vol. 9, No. 1, Jul. 1971, pp. 20-22 & 40-44, vol. 12, May 1974, pp. 73-81, A Pub. of the Hyacinth Control Soc., Ft. Lauderdale, Fla.
Chemical Abstracts, vol. 20:633$^9$ (1926), vol. 38:4661$^{2-5}$ (1944), vol. 42:2702c (1948), vol. 57:7641c (1962), vol. 80:99868a (1974) and vol. 81:90079g (1974).

*Primary Examiner*—Allen J. Robinson
*Attorney, Agent, or Firm*—Bucknam and Archer

[57] ABSTRACT

An extract containing in 100 grams about 31.641 mg. vitamin A calculated as carotene, 0.32 mg. vitamin $B_1$, 1.14 mg. vitamin $B_2$, 4.7 mg. niacin in addition to 23.2 g. protein, 4-8 g. chlorophyll, 2.30 g. crude fiber, 3.20 g. crude fats, 7.60 g. moisture, 21.50 g ash, the balance being a nitrogen-free extract, is obtained from the leaves of the tropical floating water lily or water hyacinth plant. The process of extraction is described.

The nutrients and minerals content in water hyacinth leaf or water lily leaves based on dry weight, is:

| Nutrients | Concentration, Dry Wt. |
|---|---|
| Thiamine HCl ($B_1$) | 0.591 mg. |
| Riboflavin ($B_2$) | 3.07 mg |
| Vitamin E | 10.60 mg |
| Pyroxidine HCl ($B_6$) | 1.52 mg |
| Vitamin A | 0.245 mg |
| Niacin | 7.94 mg |
| Pantothenic Acid | 5.56 mg |
| Xantophyll | 48.5 mg |
| Vitamin $B_{12}$ | 1.26 mg |
| Calcium | 7.56 mg |
| Iron | 14.30 mg |
| Phosphorous | 0.927 mg |
| Magnesium | 849.0 mg |
| Zinc | 2.3 mg |
| Copper | 0.8 mg |
| Sodium | 1.83 mg |
| Potassium | 3.60 mg |
| Sulfur | 0.45 mg |

3 Claims, No Drawings

PROCESS FOR EXTRACTING VALUABLE NUTRIENTS FROM THE LEAVES OF THE WATER LILY OR WATER HYACINTH PLANT

This application is a continuation-in-part of Ser. No. 702,612, filed July 6, 1976, now abandoned.

This invention generally relates to a process of extracting valuable nutrients of the water lily or water hyacinth, *Eichhornia crassipes* (Mart.) solms plant, consisting of vitamins, protein and chlorophyll and particularly to a product as an extract as produced by the process thereof.

The product obtained by this invention is an extract containing the valuable nutrients consisting of vitamins A and B complex or $B_1$, $B_2$ and niacin, protein and chlorophyll and has the following analysis based on 100 gram sample:

| | |
|---|---|
| Vitamin A calculated as carotene | 31.641 mg. |
| Vitamin $B_1$ | 0.32 mg. |
| Vitamin $B_2$ | 1.14 mg. |
| Niacin | 4.7 mg. |
| Protein | 23.2 g. |
| Chlorophyll | 4-8 g. |
| Crude Fiber | 2.30 g. |
| Crude Fats | 3.20 g. |
| Moisture | 7.60 g. |
| Ash | 21.50 g. |
| Nitrogen-free extract | balance |

The extract containing the vitamins, protein and chlorophyll has been utilized for deodorizing human and animal manure. Various percentages of such extract were experimented and it was found that 15% by weight is most effective to use. The odor of the manure right after secreted by the animals, such as poultry, becomes odorless if the extract in this amount is added to manure. At 10%, the result was quite good enough but there is still a slight variation at fresh secretion although the odor completely disappeared upon drying the mixture. At 5% there is still slight variation of the odor from the distinct obnoxious odor to slight foul odor.

The feeds or foods wherein 10-15% by weight of the extract are incorporated is enriched since the extract contains a protein value of about 23.2% protein. This value is considered high for a certain substance to be present. Protein is one of the very important aspects in the metabolic processes of any body either human or animal.

For human utilization in this invention, a reduced percentage is utilized since an individual has a maximum requirement for vitamin A consumption. In this case, the required amount of vitamin A for an average middle age individual is about 5,000 I.U. per day. Since 100 grams sample of the extract will give about 52,735 I.U. of vitamin A, this weight should be reduced to meet such requirements. The extract is added to the meal of the individual or molded in the form of a capsule or tablet. This capsule or tablet can be taken in before or after meals.

The extract of the present invention will help remove the obnoxious odor of human and animal waste thus, these said manures can be utilized or recycled into another major industry like fertilizer in which our country is badly in need.

The extract of the present invention will also help solve the health and sanitation problems regarding the unsanitary disposal of the human and animal manures in the sense that instead of disposing it because of its foul odor, they will store it up and make a living out of it for they can sell it to the fertilizer industry.

It is, therefore, the main object of this invention to provide a process of extracting the valuable nutrients of the water lily or water hyacinth plant, consisting of vitamins, protein and chlorophyll, and the product whenever produced by the process of the present invention.

The process of the present invention consists of letting the water hyacinth plant grow for a period of five to seven months. The plant grows well even in polluted water, except in saline water. The substances present in the water influence the composition of the final extract. It has been found that the water should have a total nitrogen content analyzed by Kjeldahl, of 9.8 kg/ha/day; total phosphorus content of 2.4 kg/ha/day. The oxygen requirement per a 5-day period is 57 kg/ha/day.

After the leaves have matured for a period of five to seven months, they are harvested, cut from the stems and allowed to wither for 48-72 hours at room temperature. At this stage the water content is 15-30%. The leaves are crushed, introduced into an expeller machine to extract the juicy substance containing the valuable nutrients present in the leaves. The juicy extract is allowed to settle in a settling tank to reduce its water content to 5-10%, the settled solids are collected and the liquid portion is discarded. The solid portion containing the extract is air-dried at temperature of 30° to 50° C. for 1 to 3 days, and the extract is pulverized in a grinding machine to a particle size that passes through a 80-120 mesh standard sieve. The pulverized extract is stored in a moisture-free container under sterile conditions. The material may be marketed as a powder in the form of capsules or tablets.

The loss in weight from the leaves to the material air dried at 30°-50° C. 1-3 days is 60-75%.

| Nutrients | Concentration, Dry Wt. |
|---|---|
| Thiamine HCl ($B_1$) | 0.591 mg. |
| Riboflavin ($B_2$) | 3.07 mg |
| Vitamin E | 10.60 mg |
| Pyroxidine HCl ($B_6$) | 1.52 mg |
| Vitamin A | 0.245 mg |
| Niacin | 7.94 mg |
| Pantothenic Acid | 5.56 mg |
| Xantophyll | 48.5 mg |
| Vitamin $B_{12}$ | 1.26 mg |
| Calcium | 7.56 mg |
| Iron | 14.30 mg |
| Phosphorous | 0.927 mg |
| Magnesium | 849.0 mg |
| Zinc | 2.3 mg |
| Copper | 0.8 mg |
| Sodium | 1.83 mg |
| Potassium | 3.60 mg |
| Sulfur | 0.45 mg |

Other components of water hyacinth leaf based on a 100 gram sample, on a dry weight are:

| | |
|---|---|
| Ash content | 20.2 g |
| Protein | 31.3 g |
| Crude Fat | 4.5 g |
| Crude fiber | 3.2 g |
| Moisture | 8.0 g |
| Nitrogen-free extract | Balance |

I claim:

1. A process for extracting from the leaves of the water hyacinth plant *Eichhornia crassipes* a product comprising vitamin A, vitamin $B_1$, vitamin $B_2$, niacin, protein and chlorophyll which comprises growing in lake or river water, which water contains oxygen in the amount of 57 kg/ha/day; the total nitrogen is 9.8 kg/ha/day; the total phosphorus is 2.4 kg/ha/day, harvesting the leaves after five to seven months growth, cutting the leaves from the stems of the said plant, collecting and withering the leaves for from 48 to 72 hours at room temperature to a water content of 30–15%, crushing the thus withered leaves, feeding the crushed leaves into an expeller machine to extract the juicy substance containing the valuable nutrients present in the leaves, allowing the juicy extract to settle to reduce its water content to 5–10%, collecting the settled solids by discarding the liquid portion, air drying the solid portion at a temperature from 30° to 50° C. for 1 to 3 days until the loss in weight is 60–75% of the weight of the leaves, to obtain an extract, pulverizing the extract to a particle size that passes through a 80 to 120 mesh standard sieve and storing under sterilized conditions and said extract contains per 100 gram sample

| | |
|---|---|
| Vitamin A calculated as carotene | 31.641 mg. |
| Vitamin $B_1$ | 0.32 mg. |
| Vitamin $B_2$ | 1.14 mg. |
| Niacin | 4.7 mg. |
| Protein | 23.2 g. |
| Chlorophyll | 4.8 g. |
| Crude Fiber | 2.30 g. |
| Crude Fats | 3.20 g. |
| Moisture | 7.60 g. |
| Ash | 21.50 g. |
| Nitrogen-free Extract | balance. |

2. The extract of the plant water hyacinth *Eichhornia crassipes* prepared by the process of claim 1.

3. The method of deodorizing animal and human manure which comprises incorporating into said manure 10–15% by weight of an extract of the plant water hyacinth *Eichhornia crassipes* as defined in claim 2.

* * * * *